United States Patent [19]

Dell'Acqua et al.

[11] Patent Number: 4,810,508

[45] Date of Patent: Mar. 7, 1989

[54] PROCESS FOR OBTAINING FOODS FREE OF LISTERIA BACTERIA

[75] Inventors: Ernani Dell'Acqua; Tiberio Bruzzese; Holger H. Van Den Heuvel, all of Milan, Italy

[73] Assignee: SPA Societa' Prodotti Antibiotici S.p.A., Milan, Italy

[21] Appl. No.: 113,068

[22] Filed: Oct. 27, 1987

[30] Foreign Application Priority Data

Oct. 28, 1986 [IT] Italy ................................ 22160 A/86

[51] Int. Cl.$^4$ ...................... A23C 9/12; A23C 19/032; A23L 1/314
[52] U.S. Cl. ........................................ 426/34; 426/36; 426/39; 426/42; 426/56
[58] Field of Search ..................................... 426/55–56, 426/34, 36, 61, 42, 39

[56] References Cited

U.S. PATENT DOCUMENTS

| 1,935,890 | 11/1933 | Rosenthal | 426/42 |
| 4,233,290 | 11/1980 | Ferrari et al. | 426/61 |

FOREIGN PATENT DOCUMENTS

| 0618088 | 8/1978 | U.S.S.R. | 426/42 |
| 0789096 | 12/1980 | U.S.S.R. | 426/42 |

Primary Examiner—Marianne Cintins
Attorney, Agent, or Firm—Oblon, Fisher, Spivak, McClelland & Maier

[57] ABSTRACT

A process for the preparation of foods of animal origin wherein efficacious quantities of lysozyme or its non-toxic salts—and optionally of synergic agents or adjuvant—are added to said foods to the purpose of obtaining foods free of Listeria bacteria.

9 Claims, No Drawings

PROCESS FOR OBTAINING FOODS FREE OF LISTERIA BACTERIA

The present invention has as its aim a process for the preparation of foods of animal origin, more precisely for the preparation of dairy and meat products and by-products.

This new process consists essentially in treating milk or meat or their semi-manufactured derivatives, with lysozyme or its non-toxic salts, optionally in presence of substances capable of exerting synergic or adjuvant action, to the purpose of thereby obtaining foods free of Listeria bacteria.

The Listeria genus, in particular the species *L. monocytogenes*, consists coccoid or rod-shaped, non-sporogenic gram-positive microorganisms, growing at temperatures ranging from 25° to 42° C.: listeriae also grow, although at a slower rate, at lower (for example 4° C.) or higher temperatures.

Listeriae are widely diffused in nature and have been identified in particular in animal and vegetable matter (in particular in silage) in milk and its derivatives, as well as in soil, waters, etc.

Listeria infections were in the past considered quite rate diseases, but in recent time listeriosis manifestations have become more and more frequent. In man, the disease may give rise to meningitis and to clinical patterns similar to those seen in infectious mononucleosis. The disease mostly affects newborn infants, pregnant women and subjects who are elderly or debilitated through various morbid forms and, hence, immunosuppressed: in the case of pregnancy, the disease may induce abortion, neonatal mortality and perinatal septicemia; sometimes in weaker subjects the outcome may even be fatal.

An evident source of infection in man may be foods of animal origin, such as milk, meat and their by-products. The disease may be transmitted by oral or urogenital route or through the faeces and urine.

In the animal world the main centres of infection can be silage, grass and waters.

On account of the growing frequency of listeriosis manifestations, studies on the transmission of the disease have recently been intensified and, for example, the possible resistance of Listeria during the pasteurization of milk has been verified.

Bearns and Girard (Can. J. Microbiol., 4, 55, 1958) found that by contaminating milk with $5 \times 10^4$ cells/ml of *Listeria monocytogenes* and then heating at 61.7° C. for 35 minutes, Listeria is not destroyed completely. If such contaminated and heat-treated milk is then stored at 22° C. for 48 hours, the surviving Listeria cells multiply up to a concentration of $10^8$ cells/ml, without producing any organoleptic alteration to the milk, while the contamination is in progress.

Further studies have demonstrated that *Listeria monocytogenes* is not only heat-resistant during pasteurization, but is also a psychrotrophic microorganism: it can in fact grow at milk refrigeration temperature.

From the above-reported fact that *Listeria monocytogenes* can resist pasteurization temperature and multiply during the milk storage period, even at the lowest preservation temperatures, it emerges that it can be of considerable risk fo the consumer and, in view of the disease being transmetted, for the public health in general.

Further studies have been performed to see whether Listeria can survive all the phases of the cheese-making process. Ryser, Marth and Doyle (J. Dairy Science, Abs. D 32, vol. 68, suppl. 1) pasteurized milk contaminated with $10^4$–$10^5$ cells/ml of *Listeria monocytogenes* (Scott A and V7 strains). During the various phases of the subsequent manufacture of cheeses, samples of manufactured and semi-manufactured products were collected, diluted in tryptose broth (TB) and, after different periods, seeded on McBrides Listeria, Agar (MLA), confirming that Listeria contamination persisted in the majority of samples.

The above-mentioned problem of listerioris does not only concern milk and its derivatives, but also all products of animal origin, e.g. meat in general and its derivatives, such as minced meat, sausage-meat, as also reported in literature.

We have now discovered that by adding suitable quantities of lysoqyme (or its non-toxic salts), to milk, meat and their semi-manufactured by-products, foods free of Listeria bacteria are obtained at the end of the working process.

We have also found that the addition of synergic or adjuvant substances, for example the alkaline salts of ethylenediamine tetra-acetic acid (EDTA), considerably increases the efficacy of lysozyme mentioned above of obtaining foods not contaminated by the aforementioned microorganisms.

It is known that lysozyme is a basic protein widely diffused in nature. The most available source is hen egg-white, where it is contained in quantities friom 0.3–0.5% and is extracted from the same in industrial quantities.

Its use in dairy produce is permetted in numerous countries to prevent late blowing in some types of cheeses, a phenomenon due to contamination of the milk with vegetative forms or spores of particular bacteria (tyrobutyric clostridia) and their successive development or germination during the cheese ripening process.

Microbiologic screenings have reported that lysozyme has a certain activity on listeriae in vitro: however no-one has ever evidenced the possibility of its practical application, and so lysozyme may be added to milk and dairy products, or to meat and its derivatives, as claimed in accordance with the present invention, with the precise intent to combat Listeria contamination, in particular by *Listeria monocytogenes*, and the consequent risk of infection by the same bacterial agent.

It is to be pointed out in this regard that listeriae are in fact sensitive to other substances, in particular to antibiotics, such as gentamicin and ampicillin, but sterilization with such agents can not be carried out unless the infection is already in progress: for obvious reasons their systematic use as prevention is not possible and neither their direct use in foods.

However this is instead possibile with lysoqyme: as previously reported lysozyme is a natural substance, present in egg-white, and as such is absolutely harmless and may be continuously swallowed with food. Besides, is does not give a particular taste or other organoleptic properties to milk or to the other foodstuffs considered above.

Other particular advantages evidenced herewith, concerning the use in the present invention, are: its stability at the temperatures used for the pasteurization of the milk process: the absence, at the doses herein defined, of any interference with the normal physico-chemical processes going on during the cheese-making process; its stability at the pH values and temperatures adopted during the cheese-making processes to obtain cooked, semi-cooked and non-cooked cheeses, as well as "pasta filata" and processed cheeses; its ability during the cheese-making process to bind to the rennet (unlike other substances tested experimentally as possible alternatives to lysozyme) and hence to the cheese, where it remains to carry out its anti-Listeria action and to preserve the food from further contaminatiion; and, finally, its excellent stability over a period of time during prolonged storage of cheese, sausage-meats and other foods described.

Obviously, the characteristics cited above, peculiar to lysozyme, also apply to its salts with non-toxic and pharmacologically acceptable acids, in particular hydrochloride and lactate, but also phosphate, glycerophosphate, citrate, ascorbate, etc., all appropriately employable in the process of the present invention and included in the appended claims.

As regards the use of lysozyme and its salts in combination with synergic or adjuvant substances, some of such substances have already been mentioned in literature following microbiological screenings carried out in vitro. In no case however has their synergic activity been evidenced in tests performed on substances of animal origin, such as milk, meat and their derivatives, neither has the possibility and the opportunity of their useful practical employment as preservatives in food, in synergism with lysozyme, ever been suggested.

In relation to the methods adopted in defining the process in object and for the opportune extensions and experimental confirmation, lysozyme activity was tested on different strains of Listeria (in particular *L. monocytogenes*) in suitable culture media and, what is more, in milk, meat and their semi-manufactured products. The stability of lysozyme was verifiedanalytically, in microbiological form suitable to exert its action on listeriae, during the storage and/or seasoning of the semi-manufactured products and in the finished foodstuffs.

In particular, the ability of lysozyme to lyse *Listeria monocytogenes* strains (different strains could be, of course, less sensible) was tested starting from cell suspensions in sodium phosphate buffer pH=6.6.

In the various tests different strains of Listeria were used:
*Listeria monocytogenes* California
*Listeria monocytogenes* Scott A
*Listeria monocytogenes* 20 A 2 Ohio
*Listeria monocytogenes* V7
*Listeria monocytiogenes* ATCC 9525 and each strain was purified so as to isolate a single colony before treatment with lysozyme. All the cultures were left to grow in an appropriate nutritional medium in optimal temperature and aeration conditions and, after one night's incubatiion, collected by centrifugation at 9,500 rpm for 20 minutes. The cell mass was then re-suspended in 0,067M sodium phosphate buffer at pH 6.6 and, after the addition of lysozyme (quantity varied according to the experiment), each test-tube was stoppered and homogenized, then the absorbance determined at 540 nm in a Bausch & Lomb Spectronic 20 spectrophotometer.

The test-tubes were then incubated in a water bath at 37° C. and the adsorbance measured again at 20–30 minute intervals for a minimum of two hours, thereby determining cellular lysis over a period of time.

Instead for the trials in milk, samples were selected which were naturally contaminated with different species of Listeria; or, more often, the milk was contaminated directly, for experimental purposes, with the same *Listeria monocytogenes* strains previously reported.

In relation to the parameters which could affect the activity of lysozyme in the different strains of Listeria, we have found that a slightly acidic pH, for example a pH ranging from 4.5 to 6.5, positively affects said activity.

This finding is noteworthy for the cheese-making processes, which usually are carried out at a pH of about 5.0.

With regard to the acidification process we have also found that, when the milk is acidified by citric acid, there is a strengthening of the activity of lysozyme on the strains of Listeria which had previously appeared to be sensible to its action. We ascrive said synergic effect to the well known chelating power of the citric acid; from that it could be deemed that numerous different chelating agents, such as EDTA and similar substances, can advantageously display the same effect of the citric acid.

Another finding of particular importance concerns the temperature which can enhance the effect of lysozyme on the different strains of Listeria. During our experiments the used temperatures have been those which are usually employed for the pasteurization processes (60°–70° C.).

Particularly, the best results are those obtained when the pasteurization is carried out in the presence of lysozyme.

The activity of lysozyme was then determined by treating the various samples of milk with different quantities of lysozyme according to the experiment. After suitable incubation the samples were seeded in comparative form, on McBrides Listeria agar, with samples not treated with lysozyme, controlling the possible presence of residual Listeriae colonies.

Analogous methods were used to determine the efficacy of lysozyme during cheese-making processes and for the various final controls on cheese, hams, sausage-meats, etc., carried out by suitably extracting food with the buffer solutions already reported.

Equally positive results were obtained during the preparation of sausage and other semi-manufactured meats, carried out with lysozyme in smaller quantities but with the addition of synergic agents such as EDTA sodium salt. With regard to the determination of lysozyme added to foods and residue after the various processes of seasoning or storage, the control was easily carried out by aqueous extraxtion and liquid phase determination of the lytic activity on *Micrococcus luteus*. This operation was able to systematically demonstrate the presence of lysozyme and its preservation in microbiologically active form.

Herebelow are reported some experimental examples which do not however limit the process of the present invention.

EXAMPLE 1

A suspension of *Listeria monocytogenes* Scott A cells was prepared in sodium phosphate buffer 67 mM pH 6.6 so as to have an absorbance of 0.650 to 540 nm.

The suspension was divided into two parts and to one part a freshly prepared lysozyme hydrochloride solution was added so as to have a final concentration of 10 $\mu$g/ml.

The two suspensions were then incubated at 37° C. on a water bath and the absorbance of the suspensions measured at various intervals. Table 1 reports the values obtained.

TABLE 1

| Incubation time in minutes | Absorbance values at 540 nm | |
|---|---|---|
| | Without lysozyme | With lysozyme |
| 0 | 0.650 | 0.640 |
| 20 | 0.640 | 0.510 |
| 40 | 0.630 | 0.450 |
| 60 | 0.620 | 0.430 |
| 80 | 0.620 | 0.400 |
| 100 | 0.600 | 0.380 |
| 120 | 0.590 | 0.350 |
| 240 | 0.580 | 0.250 |

EXAMPLE 2

A suspension of *Listeria monocytogenes* V 7 cells was prepared by centrifugation at 9500 rpm for 20 minutes.

The concentrated suspension was added to non-cooked milk so as to have a final concentration of $10^5$ cells/ml.

The inoculated milk was divided into two parts and to one part a solution of lysozyme was added so as to have a final concentration of 50 μg/ml. The two samples were heated at 62° C. for 20 minutes.

After this treatment the residual cells count was repeated by seeding and incubating the samples or diluted milk with tryptose broth in McBrides Listeria Agar. In the samples not treated with lysozyme, colonies of Listeria were evidenced that had not been destroyed by heating. Instead in the treated sample not one colony of *Listeria monocytogenes* was evidenced, even when the sample was concentrated.

This demonstrates that the treatment with lysozyme was able to lyse the Listeria cells or at least cause an impairment such as to reduce their resistance to heat.

EXAMPLE 3

100 ml of fresh milk were contaminated with *Listeria monocytogenes* (strain ATCC 9525) and added with lysozyme.

The milk was subsequently divided into two parts of each 50 ml. One part (sample B) was heated at 72° C. for 1 minute; the other (sample A) was not treated. Both samples were incubated at 37° C. for 24 hours and then kept at 4° C.

In the following Table are reported the contaminating values as microorganisms/ml.

| Sample | ppm of lysozyme | TIME AT +4° C. | | | |
|---|---|---|---|---|---|
| | | 0 hours | 24 hours | 15 days | 30 days |
| A | 100 | $3,2 \times 10^2$ | $4,3 \times 10^2$ | $1,7 \times 10^3$ | $2,5 \times 10^3$ |
| B | 100 | $3,5 \times 10^2$ | $2 \times 10^1$ | $5,0 \times 10^1$ | $1,7 \times 10^2$ |

EXAMPLE 4

A sample of milk was contaminated with *Listeria monocytogenes* (strain ATCC 9525) and subsequently divided into two parts. One parte (sample A) was kept at its natural pH (6.5). The other part (sample B) was brought to pH 5.2. Half of each sample A and B was kept as such; the other was added with lysozyme (they are named as samples $A_1$ and $B_1$ respectively).

The four samples were incubated at 37° C. for 24 hours and subsequently kept at 4° C.

The contaminating values of *Listeria monocytogenes*, as microorganisms/ml, are reported in the following Table.

| Sample | ppm of lysozyme | pH | TIME AT +4° C. | | | |
|---|---|---|---|---|---|---|
| | | | 0 hours | 24 hours | 15 days | 35 days |
| A | 0 | 6,5 | $5,0 \times 10^2$ | $3,0 \times 10^8$ | $2,3 \times 10^8$ | $7,0 \times 10^8$ |
| B | 0 | 5,2 | $5,4 \times 10^2$ | $9,0 \times 10^7$ | $2,8 \times 10^8$ | $5,1 \times 10^8$ |
| $A_1$ | 100 | 6,5 | $5,1 \times 10^2$ | $4,0 \times 10^3$ | $2,7 \times 10^3$ | $2,5 \times 10^3$ |
| $B_1$ | 100 | 5,2 | $4,2 \times 10^2$ | $3,0 \times 10^2$ | $1,5 \times 10^2$ | $1,6 \times 10^2$ |

The results reported in the Table confirm the activity of lysozyme and emphasize that its activity is enhanced at an acidic pH (5.2), a value which is in the typical range used for the cheese-making processes.

EXAMPLE 5

A sample of milk was contaminated with *Listeria monocytogenes* (strain ATCC 9525) and then divided into two parts.

One part (sample A) was brought at pH 5.2 by lactic acid; the other part (sample B) was brought to the same pH using citric acid. Half of each sample A and B was kept such; the other was added with lysozyme. They are named as samples $A_1$ and $B_1$ respectively.

The four samples were incubated at 37° C. for 24 hours and subsequently kept at +4° C.

The contaminating values of *Listeria monocytogenes*, as microorganisms/ml, are reported in the following table.

| Sample | ppm of lysozime | Acid | TIME AT +4° C. | | | |
|---|---|---|---|---|---|---|
| | | | 0 hours | 24 hours | 15 days | 35 days |
| A | 0 | Lactic | $2,9 \times 10^2$ | $3,0 \times 10^8$ | $2,3 \times 10^8$ | $7,0 \times 10^8$ |
| B | 0 | Citric | $4,2 \times 10^2$ | $5,6 \times 10^7$ | $5,0 \times 10^8$ | $6,3 \times 10^8$ |
| $A_1$ | 100 | Lactic | $1,2 \times 10^2$ | $2,4 \times 10^2$ | $8,0 \times 10^2$ | $1,5 \times 10^3$ |
| $B_1$ | 100 | Citric | $3,3 \times 10^2$ | $<10^1$ | $<10^1$ | $<10^1$ |

The obtained data put in evidence the synergic effect of the citric acid on the anti-microbic activity of lysozyme.

EXAMPLE 6

Following the traditional technology a pilot production of mozzarella, a typical "pasta filata" cheese, was performed. 200 l of milk inoculated with $2 \times 10^5$ cells/ml of *Listeria monocytogenes* California strain was used and divided into two 100 l parts. One part was used for making mozzarella cheese according to the normal process.

To the other 100 l sample of milk, inoculated with Listeria cells, a solution of lysozyme lactate was added so as to have a final concentration of 20 μg/ml, before going on to make the mozzarella.

Samples were collected during all the phases of the two work cycles and diluted with tryptose broth and seeded on McBrides Listeria agar such or after low temperature concentration.

The samples from milk not treated with lysozyme showed the presence of colonies of *Listeria monocytogenes*, whereas the samples from milk treated with lysozyme were seen to be free of the contaminating agent.

EXAMPLE 7

In taleggio cheese-manufacturing tests carried out according to the usual technology, the treatment scheme reported in the previous example was followed.

*Listeria monocytogenes strain* 20 A 2 Ohio was used as contaminating germ working so as to have in the milk a final concentration of $2 \times 10^5$ cells/ml. In the test with lysozyme the enzyme final concentration was 30 µg/ml.

In this case as well, in the test in which lysozyme was added to the milk no Listeria colonies were present, unlike the test performed without lysozyme.

EXAMPLE 8

Grana cheese-manufacturing tests were carried out following the normal technique but using a milk contaminated with $10^5$ cells/ml of *Listeria monocytogenes* V 7.

With this contaminated milk, two separate cheese-making processes were carried out: one with the contaminated milk as such and the other after lysozyme had been added up to a final concentration of 25 µg/ml.

As per the previous tests, colonies of *Listeria monocytogenes* were found in the samples without lysozyme, whereas no colonies were present in the samples treated with lysozyme.

EXAMPLE 9

Frankfurters were prepared by making two mixtures, each one made up of minced pork (3.75 kg), pork shoulder ham (22.5 kg), lardon (16.5 kg), caseinate HV (3.5 kg), salt (1.5 kg) and flavouring, and then contaminated with $10^5$ cells/g of *Listeria monocytogenes* V 7.

3.75 kg of water was added to the first mixture and 3.75 kg of a 0.7% lysozyme hydrochloride solution to the second so as to have a lysozyme concentration of about 500 µg/g in the final mixture.

The mixtures were processed according to the normal technique, packed and stored at 3° C.

Samples were collected on day 8, 20 and 40 of seasoning and the usual controls for the presence of Listeria carried out. The samples not treated with lysozyme showed the presence of numerous colonies of *Listeria monocytogenes* whereas those treated with the enzyme resulted germ-free.

EXAMPLE 10

Proceeding as reported in Example 6, two frankfurter mixtures are prepared and contaminated with $10^5$ cells/g of *Listeria monocytogenes* V 7. 3.75 kg of water is added to the first and 3.75 kg of a 0.35% lysozyme hydrochloride solution and a 1.4% EDTA sodium salt solution to the second so as to have concentrations of 250 µg/g and 1000 µg/g respectively in the final mixture.

Proceeding as reported in Example 6, the complete elimination of the contaminating agent is obtained only in the product treated with lysozyme and EDTA.

EXAMPLE 11

200 battery chickens were slaughtered and half of the batch placed in cold storage after the normal work cycle. The other half was subjected to spray treatment with a solution of 100 g lysozyme per quintal of water before being placed in the same cold storage.

At various intervals 20 subjects at a time removed from the two batches and controlled for presence of Listeria. By totaling the results obtained is was possible to evidence that on the whole 3.5% of the chickens not treated showed presence of the microorganism, unlike those treated with lysozyme that resulted totally absent.

We claim:

1. A process for the treatment of foods to achieve freedom from Listeria bacteria, which comprises adding in an acidic environment of pH 4.5 to 6.5 an efficacious quantity of lysozyme or its non-toxic salt to a dairy or meat product in an amount sufficient to achieve said Listeria-free foods.

2. A process according to claim 1, wherein the dairy product is milk, cheese, cream, butter, ice cream or fermented milk.

3. A process according to claim 1, wherein the meat product is ham or sausage.

4. A process according to claim 1, wherein lysozyme or its non-toxic salt is added to lyse Listeria bacteria cells present as contaminants in foods.

5. A process according to claim 1, wherein lysozyme or its salt is added to preserve foods from contamination by Listeria during a seasoning or storage stage.

6. A process according to claim 1, wherein the non-toxic salt of lysozyme is hydrochloride, lactate, phosphate, glycerophosphate, citrate, or ascorbate.

7. A process according to claim 1, wherein the efficacious quantity of lysozyme or its non-toxic salt is 5–500 ppm with respect to the food to which it is added.

8. A process according to claim 1, further comprising effective amounts of alkaline salts of ethylenediamine tetra-acetic acid (EDTA) or citric acid.

9. A process according to claim 1, wherein the foods obtained are free from bacteria of the *Listeria monocytogenes* species.

* * * * *